United States Patent
Schardey

(10) Patent No.: US 11,793,409 B2
(45) Date of Patent: Oct. 24, 2023

(54) SYSTEM FOR THE EARLY DETECTION OF POSTOPERATIVE BLEEDING

(71) Applicant: ISAR-M GmbH, Holzkirchen (DE)

(72) Inventor: Anne Schardey, Gmund (DE)

(73) Assignee: ISAR-M GmbH, Holzkirchen (DE)

( * ) Notice: Subject to any disclaimer, the term of this patent is extended or adjusted under 35 U.S.C. 154(b) by 125 days.

(21) Appl. No.: 16/337,969

(22) PCT Filed: Sep. 15, 2017

(86) PCT No.: PCT/EP2017/073366
§ 371 (c)(1),
(2) Date: Mar. 29, 2019

(87) PCT Pub. No.: WO2018/059975
PCT Pub. Date: Apr. 5, 2018

(65) Prior Publication Data
US 2020/0022593 A1 Jan. 23, 2020

(30) Foreign Application Priority Data
Sep. 30, 2016 (DE) ................... 10 2016 118 673.2

(51) Int. Cl.
*A61B 5/02* (2006.01)
*A61B 5/0205* (2006.01)
(Continued)

(52) U.S. Cl.
CPC ........ *A61B 5/02042* (2013.01); *A61B 5/0205* (2013.01); *A61B 5/036* (2013.01);
(Continued)

(58) Field of Classification Search
CPC ... A61B 5/02042; A61B 5/0205; A61B 5/036; A61B 5/14542; A61B 5/7267;
(Continued)

(56) References Cited

U.S. PATENT DOCUMENTS 5,724,983 A * 3/1998 Selker ................... A61B 5/412
600/301
5,788,642 A * 8/1998 Hamatake .............. A61B 5/031
600/561
(Continued)

FOREIGN PATENT DOCUMENTS

CN 101194271 A 6/2008
CN 105787285 A 7/2016
(Continued)

OTHER PUBLICATIONS

International Search Report dated Dec. 22, 2017 in PCT/EP2017/073366 filed on Sep. 15, 2017.
(Continued)

*Primary Examiner* — Amanda K Hulbert
*Assistant Examiner* — Natasha Patel
(74) *Attorney, Agent, or Firm* — Christopher A. Rothe; Culhane Meadows PLLC

(57) ABSTRACT

The invention relates to a system for the early detection of invalidating states of persons, such as a postoperative bleeding of a patient for example, in particular secondary bleeding after organ surgery, comprising a detector unit (30) for continuously detecting multiple selected parameters. The detector unit has sensors (14, 16, 18), a computing unit, an interface and an analysis logic which evaluates the probability of the presence of a health anomaly, such as the probability of postoperative bleeding for example, on the basis of the present parameter states. Additionally, a display device (40) is provided by means of which the evaluation is displayed. The pressure in the postoperative organ compartment and/or a parameter which represents the expansion of the section of the skin adjoining the organ compartment is selected as the selected parameter.

20 Claims, 11 Drawing Sheets

(51) Int. Cl.
*A61B 5/03* (2006.01)
*A61B 5/145* (2006.01)
*A61B 5/00* (2006.01)
A61B 5/021 (2006.01)
A61B 5/024 (2006.01)
A61B 5/08 (2006.01)

(52) U.S. Cl.
CPC ........ *A61B 5/14542* (2013.01); *A61B 5/7267* (2013.01); *A61B 5/7275* (2013.01); *A61B 5/7425* (2013.01); A61B 5/021 (2013.01); A61B 5/024 (2013.01); A61B 5/0816 (2013.01); A61B 2560/0223 (2013.01); A61B 2562/0247 (2013.01)

(58) Field of Classification Search
CPC ..... A61B 5/7275; A61B 5/7425; A61B 5/021; A61B 5/024; A61B 5/0816; A61B 2560/0223; A61B 2562/0247; A61B 2562/0261; A61B 5/1073
See application file for complete search history.

(56) References Cited

U.S. PATENT DOCUMENTS

| | | | |
|---|---|---|---|
| 9,750,429 | B1 | 9/2017 | Sackner et al. |
| 10,943,692 | B1* | 3/2021 | Lynn ................ G06T 11/206 |
| 2002/0032386 | A1 | 3/2002 | Sackner et al. |
| 2002/0072647 | A1* | 6/2002 | Schock ............... A61B 5/0215 600/18 |
| 2003/0135127 | A1 | 7/2003 | Sackner et al. |
| 2005/0283092 | A1 | 12/2005 | Gedebou |
| 2006/0079773 | A1* | 4/2006 | Mourad ................. A61B 5/031 600/438 |
| 2006/0241728 | A1* | 10/2006 | Vamanrao ............ A61B 1/3132 607/92 |
| 2006/0264775 | A1* | 11/2006 | Mills ..................... A61B 5/308 600/509 |
| 2006/0276726 | A1 | 12/2006 | Holsten |
| 2007/0093721 | A1* | 4/2007 | Lynn ..................... G16B 45/00 600/324 |
| 2008/0312543 | A1 | 12/2008 | Laufer et al. |
| 2010/0231377 | A1 | 9/2010 | Sandholdt |
| 2011/0087115 | A1 | 4/2011 | Sackner et al. |
| 2011/0087117 | A1* | 4/2011 | Tremper ............ A61B 5/02055 600/508 |
| 2011/0319724 | A1* | 12/2011 | Cox ..................... A61B 5/7264 600/301 |
| 2012/0041279 | A1* | 2/2012 | Freeman ................ G16H 20/40 600/301 |
| 2012/0165621 | A1 | 6/2012 | Grayzel et al. |
| 2013/0137941 | A1* | 5/2013 | Schardey ............. A61B 5/0004 600/301 |
| 2013/0231584 | A1* | 9/2013 | Burnett .................. A61B 5/036 600/561 |
| 2014/0012120 | A1* | 1/2014 | Cohen ................ A61B 5/02042 600/371 |
| 2014/0275835 | A1* | 9/2014 | Lamego ............... A61B 5/0022 600/480 |
| 2015/0305632 | A1* | 10/2015 | Najarian .............. A61B 5/7207 600/479 |
| 2015/0313512 | A1 | 11/2015 | Hausman et al. |
| 2016/0038042 | A1* | 2/2016 | Mulligan ............... A61B 5/031 600/371 |

FOREIGN PATENT DOCUMENTS

| | | |
|---|---|---|
| CN | 105848568 A | 8/2016 |
| DE | 10 2013 200 806 A1 | 7/2014 |
| EP | 2 377 460 A1 | 10/2011 |
| JP | 2000-93398 A | 4/2000 |
| JP | 2013-535995 A | 9/2013 |
| JP | 2014-502854 A | 2/2014 |
| KR | 10-2013-0058007 A | 6/2013 |
| KR | 10-2013-0140616 A | 12/2013 |
| WO | WO 2007/097635 A1 | 8/2007 |

OTHER PUBLICATIONS

German Search Report dated May 5, 2017 in German Application 10 2016 118 673.2 filed on Sep. 30, 2016 (with unedited computer-generated English translation).
Combined Chinese Office Action and Search Report dated Jun. 28, 2021 in Chinese Patent Application No. 201780060919.1 (with unedited computer generated English translation), 20 pages.
Japanese Office Action dated May 10, 2021 in Japanese Patent Application No. 2019-538712 (with English translation), 11 pages.
Korean Office Action dated Oct. 29, 2021in KR Application No. 10-2019-7012630, filed Apr. 30, 2019 w/English translation.
Office Action dated Mar. 15, 2022, in Chinese Patent Application No. 201780060919.1 filed Sep. 15, 2017 (with machine English translation).
Office Action dated Mar. 7, 2022, in Japanese Patent Application No. 2019-538712 (with English translation).
Combined Chinese Office Action and Search Report dated Jan. 11, 2023 in Chinese Patent Application No. 201780060919.1, 7 pages.

* cited by examiner

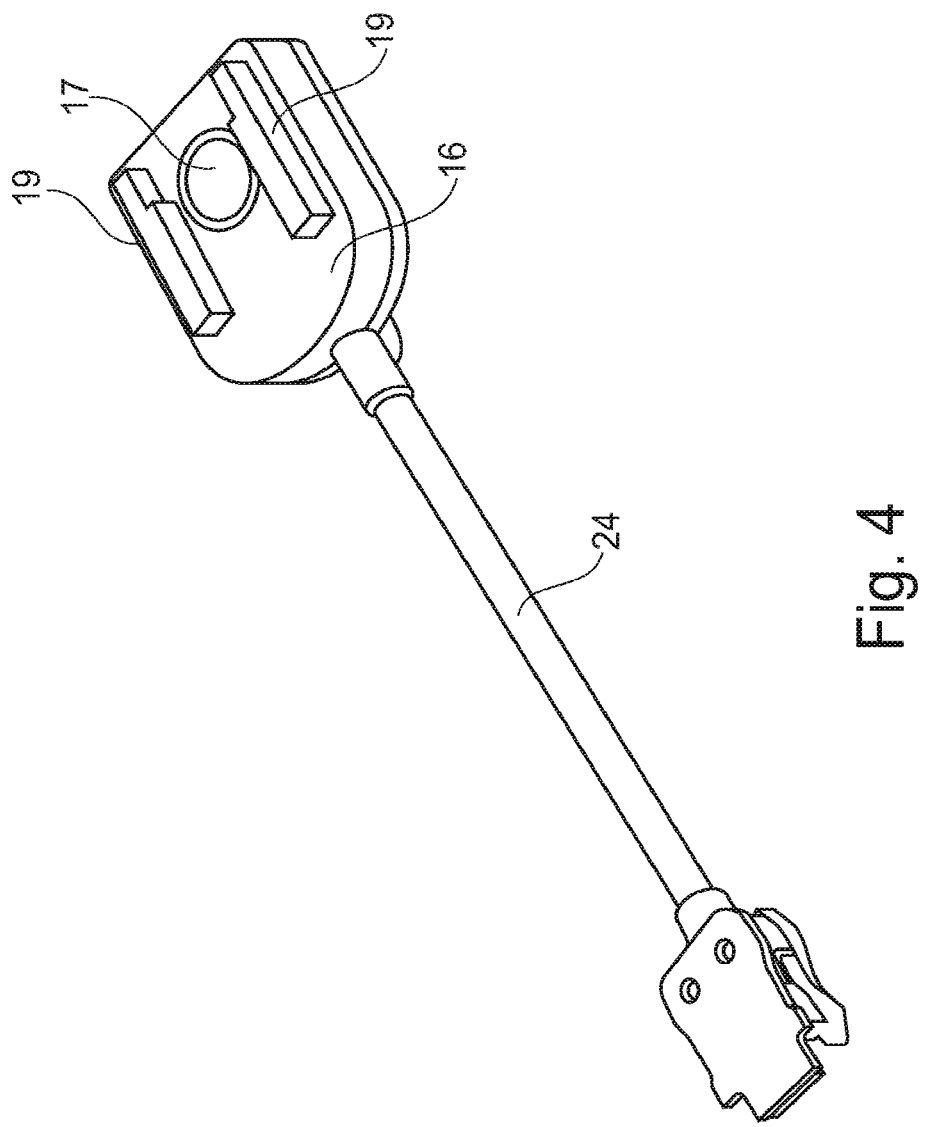

SYSTEM FOR THE EARLY DETECTION OF POSTOPERATIVE BLEEDING

The invention relates to a system for the early detection of invalidating states of persons, such as for the early detection of postoperative bleedings, especially of secondary bleedings in the case of organ surgeries such as e.g. a thyroid surgery.

Monitoring systems are well-known in various configurations which are preferably used in hospitals for patient monitoring. Accordingly, frequently merely relevant vital parameters such as e.g. pulse, heart rate etc. are monitored, with an alarm being triggered when the respective static limits of the vital parameters are exceeded. Examples of said monitoring systems are described in the documents US2011/0160549 A1, US 2005/0187796 A1 or US 2004/0143174 A1.

There are also systems by which predictions of critical states may be made. For this purpose, in the system according to US 2011/0282169 A1 inter alia the brain pressure is monitored. In US 2008/0287753 A1 a system is described in which different parameters are detected and analyzed, wherein particular states of the patient are concluded from the parameter constellation.

However, in the postoperative course various complications such as e.g. shock, heart attack, pulmonary embolism as well as bleedings may occur which do not show by trivial exceeding of limits of individual vital parameters. Such secondary bleedings, especially secondary bleedings after thyroid surgeries, are extremely dangerous, as they may result in sudden breathing arrest.

A generic system is known, for example, from the document EP 2 377 460 B1, the content of disclosure of which concerning the parameter evaluation is herewith fully incorporated in the present application. By said system insignificant hematomas can be reliably distinguished from the internal secondary bleeding so as to detect as early as possible the risk of bleeding to death and, resp., of the compression of vital organs.

For finding the known system use is made of the realization that the automatically operating system easily succeeds, with appropriate selection of the vital parameters to be monitored and with appropriate classification of the measured parameters into the states to be inquired, in establishing a probability about the state of the person to be monitored, wherein definite delimitation between life-threatening states, on the one hand, and rather non-critical states, on the other hand, is possible.

It is the object of the present invention to further improve the system in such manner that with a simplified structure it is capable of safely and reliably protecting the patient against the consequences of postoperative secondary bleeding.

This object is achieved by the system according to claim 1. According to the invention, it was found that the salient parameter for detecting and predicting postoperative bleeding is the pressure in the body compartment in the field of operation. Comprehensive examinations resulted in the finding that in the case of thyroid surgeries complete loss of deliberate breathing occurred when the compartment pressure had increased above a particular threshold. The selection of parameters according to the invention protects the patient with reliability not reached so far and with a simplified structure of the system against the consequences of postoperative bleeding, for example after thyroid surgery, wherein already continuous monitoring of one parameter is sufficient for this purpose. The second parameter then fulfils an additional control function.

Advantageous developments are the subject matter of the subclaims.

When, according to claim 2, data about breathing are included, the system obtains additional options for designing the analysis logic. In this way, monitoring may be further refined by including the data of breathing in the operating mode of parameter monitoring and in the analysis.

By the number of parameters monitored and/or the number of the states, such as e.g. very low, low, medium, high, very high, which can be assigned to the parameters measured, the operating mode of the system cannot only be further refined at will but also adapted to the respective individual reaction patterns of the persons to be monitored. The display device by which the evaluation is displayed is advantageous, because, on the one hand, it may be utilized to signal to the person to be monitored a state which is critical to said person, and it can simultaneously be used to communicate the result of evaluation to a hospital or to an attending physician, for example, in such a way that life-saving measures can be taken as quickly as possible.

Basically—as in the known system according to EP 2 377 460 B1 already—any unit which is capable of detecting the selected parameters may act as detector unit. As the detector unit includes measuring probes, a computing unit as well as an interface, the system is configured in such manner that it may be carried on the body of the person to be monitored as a body-related compact system. The computing unit converts the input signal of the measuring probe so that it becomes visible, for example, on an external device via an interface. The advantage of the interface resides in the fact that, on the one hand, in a case of emergency the vital parameters of the person to be monitored can be quickly rendered visible to a person skilled in the art, such as a physician, and that, on the other hand, the system may be read out with minimum effort in routine checks.

The analysis logic is preferably programmed on the basis of empirically obtained and medically established anatomic contexts. In this way, parameter constellations which occur—e.g. when coughing or in other spontaneous body reactions—only briefly are removed from the evaluation.

Preferably, the analysis logic includes a neural network by means of which parameter patterns trained in advance are recognized.

Advantageously, the early detection system is additionally capable, with the aid of the analysis logic, to produce an instruction of the content, based on the vital parameters and parameter states detected, especially with consideration of the time course thereof, as to how the person to be monitored has to be treated. Thus, it corresponds to individual recommended actions adapted to the given situation either for the person to be monitored him-/herself or for third persons, e.g. for an attending physician or a first aider who meets the person to be monitored in a critical state. Since said recommended actions are automatically generated in response to the parameter constellation detected, they may be utilized even if the person to be monitored is no longer able to provide any information. Consequently, in a case of emergency, valuable time can be gained between the diagnosis and the beginning of treatment.

Depending on the type of display device, the instruction can be displayed at least partially. This enables primarily the person to be monitored to evaluate his/her own state and not to be unnecessarily worried in a state that is not life-threatening. Otherwise, the instruction in a life-threatening state may be, inter alia, to forthwith inform an emergency physician. In parallel, concrete instructions may be displayed as to how the person has to be treated. Thus, for example the arriving physician can immediately start with the correct treatment. This results in great saving of time as said physician neither has to examine the person to be monitored nor has to spend additional time for finding the diagnosis. Moreover, as the early detection system knows the medical history of the person to be monitored, the instruction of the system corresponds to the instruction a general practitioner who is familiar with the medical history would give. Should specific apparatuses which are not part of the apparatuses carried along as a standard by the emergency physicians be required for the treatment of the person to be monitored, again valuable time can be gained by an instruction indicating said circumstance.

A neural network according to claim 7 is beneficial when a plurality of parameters has to be monitored and evaluated. Such analysis logic of the system further is capable of quickly handling a quite large number of parameter constellations and of identifying possible life-threatening states without any delay. Moreover, further parameter constellations defined by clinical research can be conveyed to the neural network by training, for example. In this way, even more precise delimitation of the parameter constellations between an insignificant state and a life-threatening state is possible.

When the parameters are detected being clocked at predetermined time intervals (dt) which are preferably adapted to the health state of the patient, the system can be used in an especially energy-saving manner, thus allowing a long service life to be achieved.

The system can be especially attractive when variable time intervals (dt) are used for detecting the parameters. Said feature enables the system to vary the intervals between two measuring points in response to the circumstances so that the time intervals can be adapted to the current health state of the patient while the system is in use. In this way, the time intervals become shorter, for example, when the state deteriorates and become longer when the state improves. The time intervals (dt) may thus become longer also in non-critical phases such as when the patient is sleeping so as to enable energy-saving operating mode again. It is also possible to vary or adapt the time intervals on the basis of the variation of further monitoring parameters.

By the development of claim 8 in which the analysis logic is based on a fuzzy logic approach instead of, as usually, on a binary digital approach, the monitored parameters do not necessarily have to be assigned to one out of two possible contrary states but also to any intermediate values, wherein the operating accuracy of the system can be increased and the number of recognizable states of the person to be monitored can be increased. The appropriate logic is obtained, for example, by clinical studies with a sufficient number of patients.

The better the system is adapted to the patient, the more efficiently and accurately it can operate. Therefore, it is of advantage when the system is trained with individual medical data of the person to be monitored. For example, the critical thresholds for the organ compartment pressure are higher in young patients than in elderly patients. In this way, the system is capable of distinguishing even more precisely between a critical health state and non-critical states such as a resting phase or a short stress phase, especially when the parameters measured are considerably different from person to person. The distinction results in the fact that considerably fewer false alarms are indicated and, resp., reported.

The development illustrated in claim 10 helps to individually calibrate the fuzzy logic module of the analysis logic in advance corresponding to the health state of the person to be monitored. Thus, possible adaptation cycles at the beginning of use are dropped and the patient is monitored at the best from the very beginning.

In order to continuously improve the system during use and to adapt it to the individual states of the patient during the time of use thereof, the analysis logic may be configured to be adaptive. This offers the advantage that the system may adapt to habits and to the rhythm of the patient during use. This helps to detect individual vital parameters and the relation thereof relative to each other, which, in turn, allows to make more exact statements concerning insignificant states such as e.g. sleeping phases or short-term efforts, as compared to life-threatening states such as postoperative bleedings, for example.

When an evaluation of the probability of the presence of a health anomaly according to claim 12 is displayed, the result of monitoring can be very easily detected. The display unit has the possibility of signaling different stages of health hazards e.g. optically by means of signal lamps of different colors. This serves for better assessment of the alarm triggered, as a life-threatening state can be displayed to be clearly differentiated from merely slightly increased values. In turn, the patient is prevented from unnecessarily worrying, which finally causes further deterioration of the health state to be avoided. In addition, false alarms and expenses unnecessarily incurred thereby can be avoided.

By the development of claim 13 at least one selected result of evaluation and/or an instruction how to handle the current state of the person to be monitored can be forwarded to a central unit by a transmitter. For transmission a Bluetooth or WLAN module can be used, for example. In this way, appropriately skilled persons can directly analyze the result of evaluation and can take actions, where necessary.

In order to be able to determine the spatial and, resp., geographic position of the person to be monitored, the transmitter may include a position detector. Said position detector is configured so that it is preferably adapted to continuously determine the position of the person to be monitored.

The transmitter may be configured so that it forwards the particular spatial and, resp., geographic position of the person to be monitored to a central unit. Consequently, the person to be monitored can be immediately found if a life-threatening state has occurred, even if said person cannot call attention to him-/herself. This allows to gain valuable time both in finding the room of a stationary patient as well as of outpatients, for example.

The system according to the invention may also be equipped with an interface which enables connection to a cell phone. On the one hand, a determination of position can be carried out by the cell phone even at locations where conventional systems such as GPS do not work and, on the other hand, the cell phone can be used to forward information.

Particular practicability and simple taking into operation are resulting when the system according to claim 15 is composed of plural functional modules which are positioned at optimal points on the body and can be separately handled. In this way the individual components are light and can be conveniently carried. The system may easily have a wireless design which especially facilitates carrying the system on the user's body, for example on the user's wrist, belt or the like.

Hereinafter, an example embodiment of the invention will be illustrated in detail by way of schematic drawings, wherein:

FIG. 4 shows a perspective view of a pressure transducer including a connecting signal cable to a signal node;

FIGS. 8 to 10 shows schematic front views of an area in which the thyroid of the human being is located, with FIG. 8 showing the state before surgery, while FIGS. 9 and 10 show the states after partial and complete organ removal.

Figure 1:
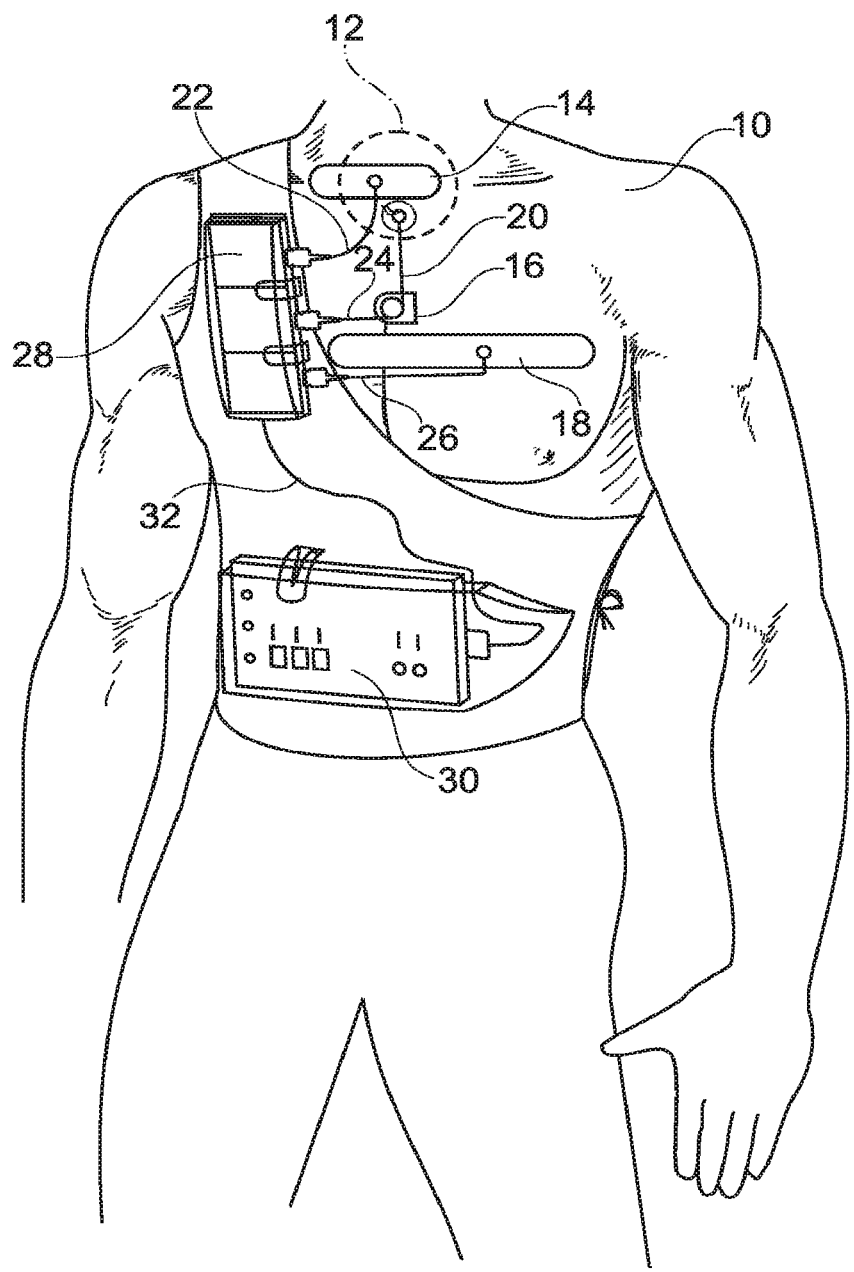
FIG. 1 shows a schematic view of the system carried by the patient for early detection of secondary bleeding after thyroid surgery.
Figure 2:
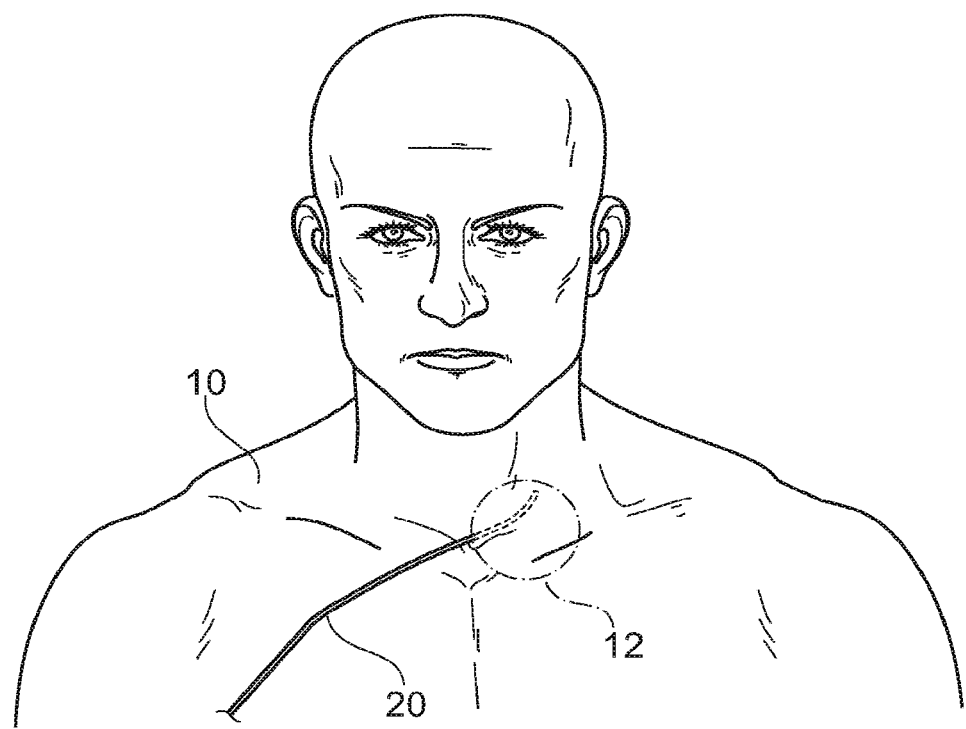
FIGS. 2 and 3 show a schematic front view and a side view of a patient including a pressure transmission tube laid to an operating field.
Figure 3:
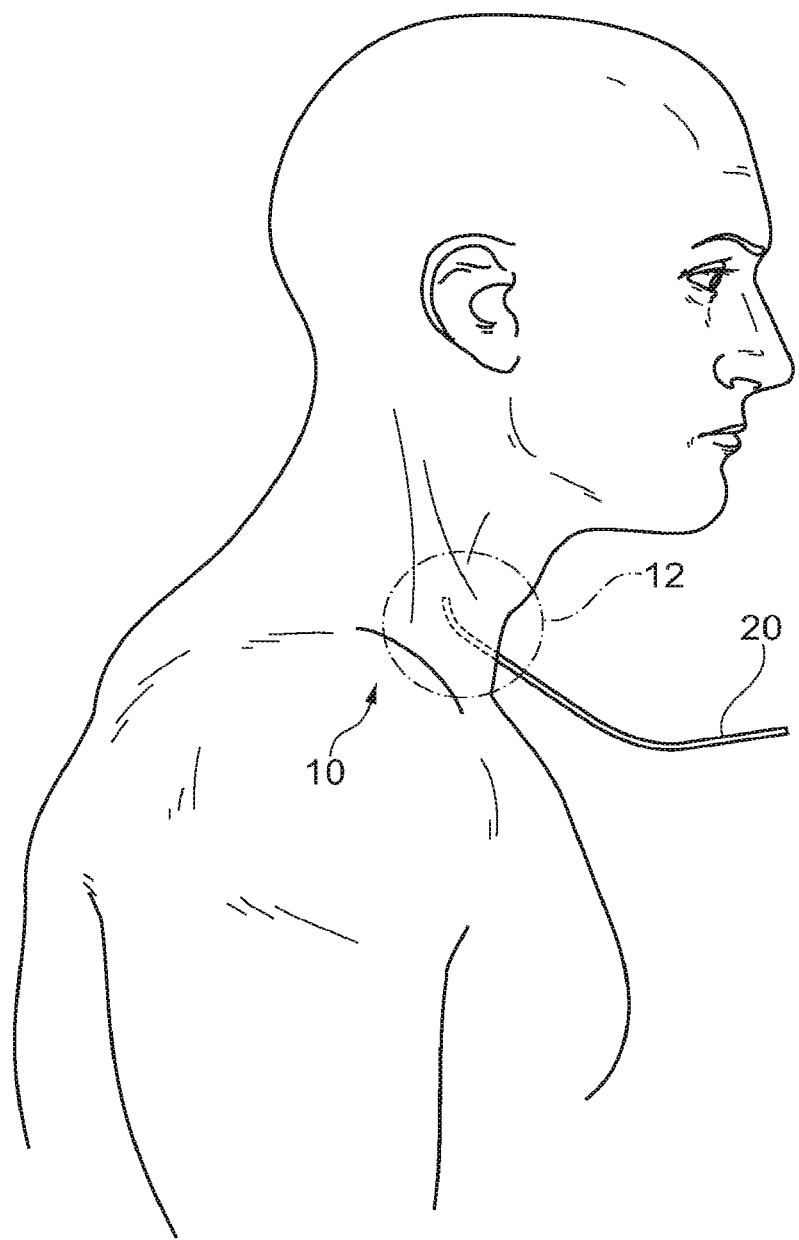

In FIGS. 1 to 3, the reference numeral 10 schematically denotes a person to be monitored (hereinafter referred to as person). It is a person who has been subjected to a thyroid surgery so that the schematically indicated operating field 12 is located in the neck area.

For detecting the parameters required to predict secondary bleeding in this embodiment three sensors and, resp., measuring probes 14, 16 and 18 are used.

The sensor 14 is formed by a tension sensor by which the expansion of the skin of the patient at a skin section located in the vicinity of the organ compartment not shown in detail, i.e. close to the operating field 12, can be detected. Alternatively, also a sensor for measuring the neck circumference could be used. Both parameters have in common that they form a measure for the swelling of a body portion adjoining the operating field.

Figure 1A:
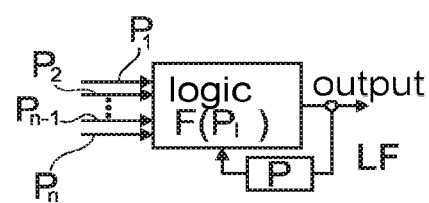
FIG. 1A shows a block diagram of the analysis logic.
Figure 1B:
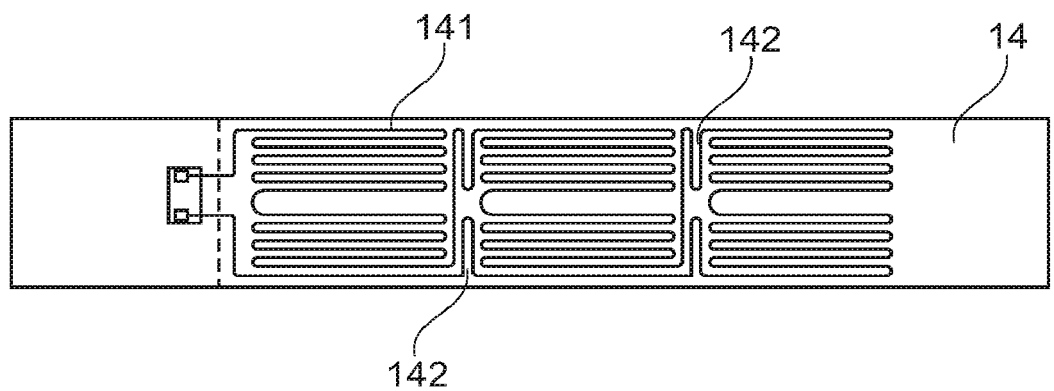
FIG. 1B shows a detailed view of the sensor for detecting the parameter depicting the skin expansion in the vicinity of the operating field.

In the shown example embodiment, the neck expansion sensor—as shown in FIG. 1A—is structured as follows: it consists of elastic support material to the surface of which a constantan wire 141 has been applied. The ends of the constantan wire are integrated—similarly to a strain gauge measurement—in an evaluating circuit, for example a bridge circuit, in a known way.

In order to render the expansion sensor capable of optimally absorbing the forces, the sensor is cast in silicone rubber having defined Shore hardness A, different materials and a specific material thickness. The dimensions of the example embodiment tested were 16.6×3 cm having a wire length of L=1.681 m. The sensor is sufficiently tightly fixed—as shown in FIG. 1—at the neck of the patient by means of known techniques and, where necessary, additional aids so that the constantan wire may adapt to the changes in shape and/or length of the skin.

When the sensor is pulled in the longitudinal direction, the total length of the constantan wire 141 varies/is extended. This results in a thinner cross-section of the constantan wire (e.g. instead of 50 µm now only 49 µm), which causes the total resistance to increase. The increase in resistance thus is directly proportional to the force in the longitudinal direction which in turn can be assigned to the expansion.

In addition, in the central area there are provided twisted meandering wire structures 142—as is evident from FIG. 1A—which in the case of higher forces have a compensating effect and to a smaller extent can also absorb transverse forces.

The measuring result can be even further increased by a layer model, in such case the bulging of the expansion sensor acting on the longitudinal expansion. The expansion sensor thus measures the change of resistance of the constantan wire which corresponds to the expansion of the sensor strip.

The sensor 16 is a pressure sensor by which the pressure within the organ compartment can be detected. In detail, a signal tube 20 leading to a balloon sewn in the organ compartment and being filled with pressure-transferring fluid, for example a liquid such as a saline solution (NaCl) is connected to the pressure transducer 16 which is known per se. Instead of a balloon, it is sufficient when the signal tube 30 is equipped at its distal end in the organ compartment with a thin-walled end cap via which the pressure in the organ compartment can be picked up.

Figure 4A:
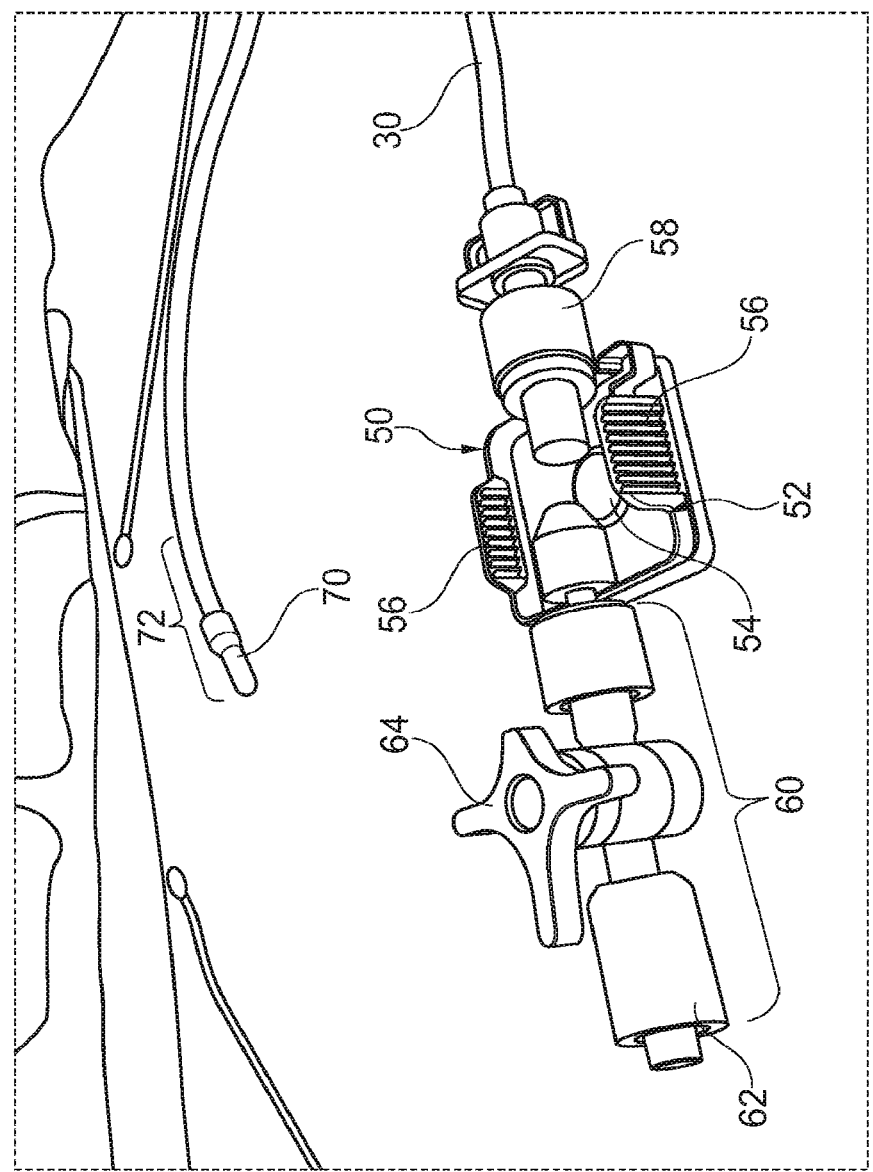
FIG. 4A shows a perspective view of a connecting piece by which a pressure signal tube can be connected to the pressure transducer.
Figure 5:
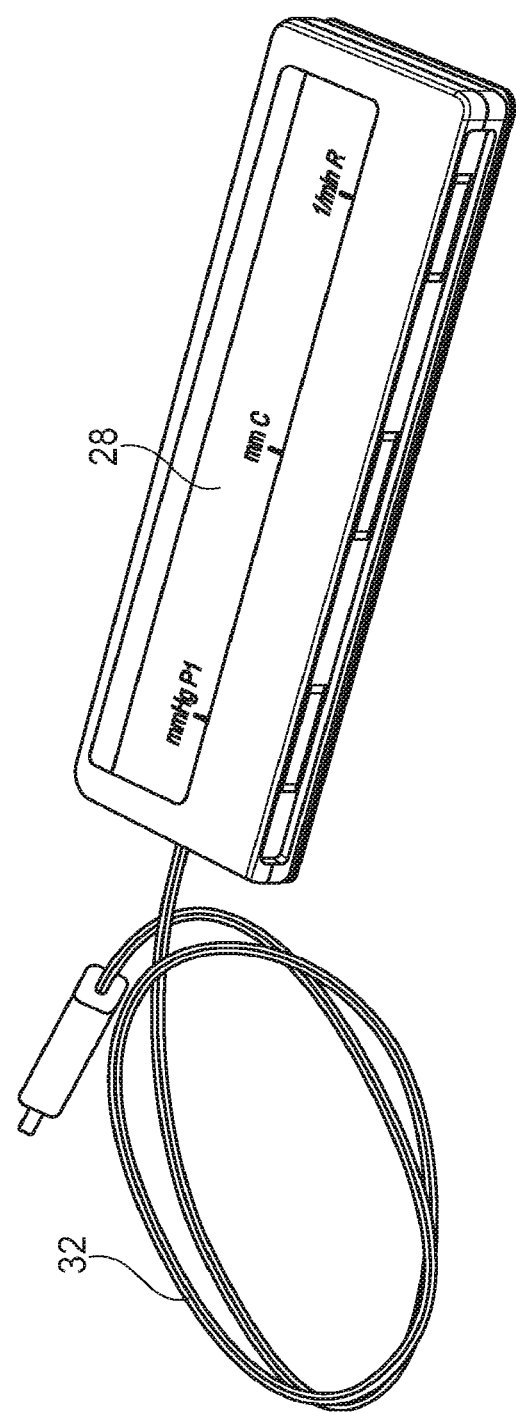
FIG. 5 shows a perspective view of a signal node including a signal connecting cable to a basic device.

In FIG. 4A a connecting piece 50 is shown by which the signal tube 30 can be connected to the pressure transducer 16. The connecting piece 50 includes a central member 52 in which a pressure transfer chamber including a pressure transfer membrane 54 is located which in the mounted state of the connecting piece 50 is in tight surface contact with the pressure sensor membrane 17 (cf. FIG. 4) of the pressure sensor. Handle portions denoted with 56 are provided for inserting and locking the connecting piece 50 in the rails denoted with 19 at the pressure transducer.

The signal tube 30 is connected to a coupling piece 58 of the connecting piece 50. When plural organ compartments are intended to be monitored, the coupling piece 58 is appropriately designed, for example as a Y coupling. On the other side of the connecting piece 50, the central member 52 bears a filling piece 60 comprising a feed connection 62 and a stop valve 64.

Reference numeral 70 denotes an end cap of the signal tube 30. The end cap 70 is preferably formed by a thin-walled plastic material and seals the lumen in the signal tube 30 in a pressure-tight manner.

In preparation of the parameter monitoring, a distal end portion 72 of the signal tube 30 is sewn into the organ compartment. For enabling pressure detection to take place, the signal tube must be filled with liquid—preferably a NaCl solution—in a bubble-free manner. Filling may be but need not be carried out in such a way that in the signal tube a particular preferably low preliminary pressure is reached. For this purpose, the connecting piece 50 is attached to the pressure sensor 16, the stop valve 64 is opened and the signal tube 30 is filled by means of a syringe via the feed connection 62 and the coupling piece 58. When the signal tube is filled, the stop valve 64 is closed and the syringe can be removed.

The third sensor 18 is formed by a strain gauge fixed e.g. to the chest or the belly of the patient 10 for detecting the breathing rate.

In this context, it is to be emphasized that the concept according to the invention already works reliably with one of the sensors 14 and 16. The more additional sensors are provided, the more possibilities of adapting the functioning of the sensors to the states of the patient and of optimizing the evaluation of the sensor signals—advantageously with the aid of an analysis logic processing all signals—are existing.

In the illustrated example configuration, the signals of the sensors are guided via signal lines 22, 24 and 26 to a signal node 28 which is separately fixed to the patient close to the operating field 12. In the illustrated example configuration, the data transmission from the signal node 28 to a basic device 30 is carried out via a signal cable 32. However, it is equally possible to carry out wireless data transmission, for example via Bluetooth or any other transmission technology.

In the basic unit an interface not shown in detail and an ECU or, resp., CPU are integrated. The interface mainly has two functions. On the one hand, it serves as a type of internal interface of the detector unit for the vital parameters detected by the measuring probes 14, 16 and 18. On the other hand, it may be an external interface for connecting external devices such as a computer or a monitor, for example.

The ECU/CPU of the basic unit 30 includes a clock generator and carries out all computing processes. Depending on the parameter and the state of the person to be monitored, the time intervals between two measuring times may considerably deviate from each other.

Further, the ECU/CPU may be equipped so that it can access a memory in which all relevant instructions as to how the person to be monitored has to be treated on the basis of the currently given parameters are stored. Accordingly, the memory may be both an internal memory and an external memory. In the same, the ECU/CPU can store both the instructions for being read out when needed and the courses or developments of the courses of parameters over rather long periods. They can be read out and analyzed via the interface during routine checks, for example.

The analysis logic of the ECU/CPU corresponds to the block diagram according to FIG. 1A. The input variables of the sensors are represented by $P_1$ to $P_n$, the analysis logic is represented by $F(P_i)$, the return path for adaptability is represented by the designation LF and the processing of the result for adapting the analysis logic for future evaluations is represented by the designation P.

For utilizing the system, for example in thyroid surgery, it is processed as follows.

Figure 7:
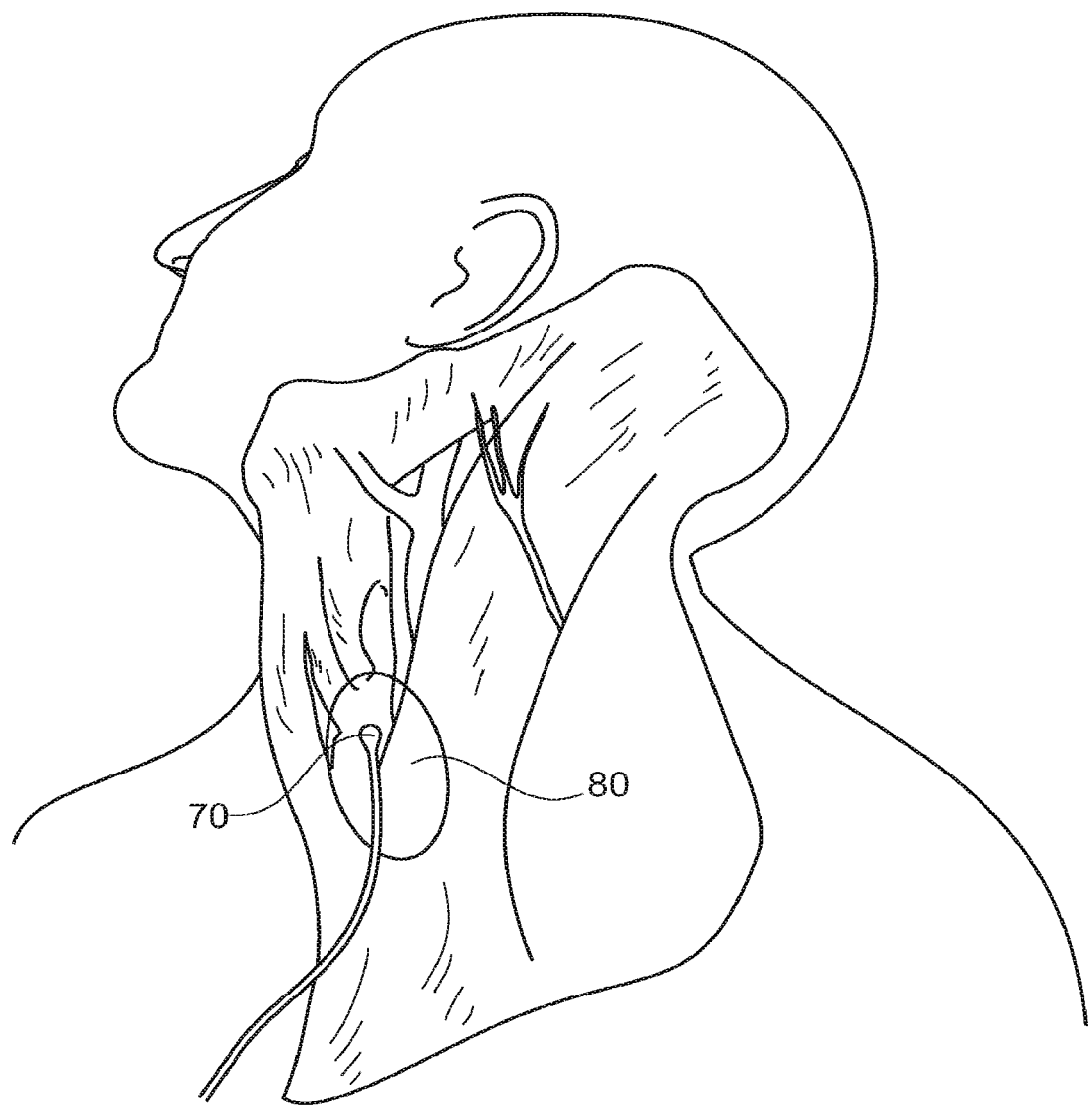
FIG. 7 shows a schematic perspective view of the neck part of a patient to illustrate the position of a thyroid compartment including an inserted pressure sensor.

When—as schematically indicated in FIG. 7—the thyroid has been removed, in the forming thyroid compartment 80 the distal end of the signal tube 30 including the end cap 70 enclosing the pressure-tapping chamber is positioned. This part of the signal tube 30 is sewn into the patient, for example, or, in the case of minimal-invasive operating technique, is fixed otherwise in the patient's body so that the end cap 70 including the pressure-tapping chamber is fixed in the organ compartment 80.

Figure 8:
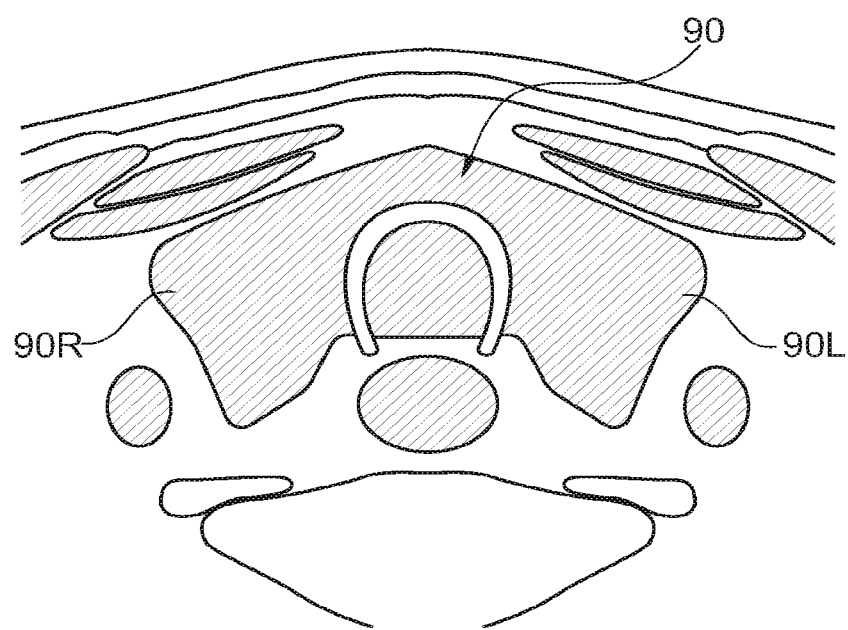
Figure 9:
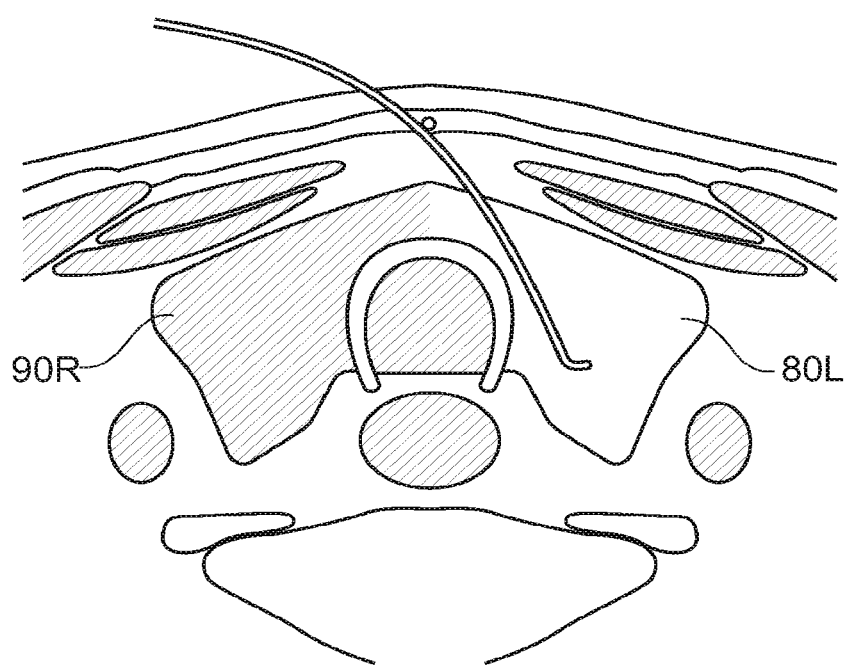
Figure 10:
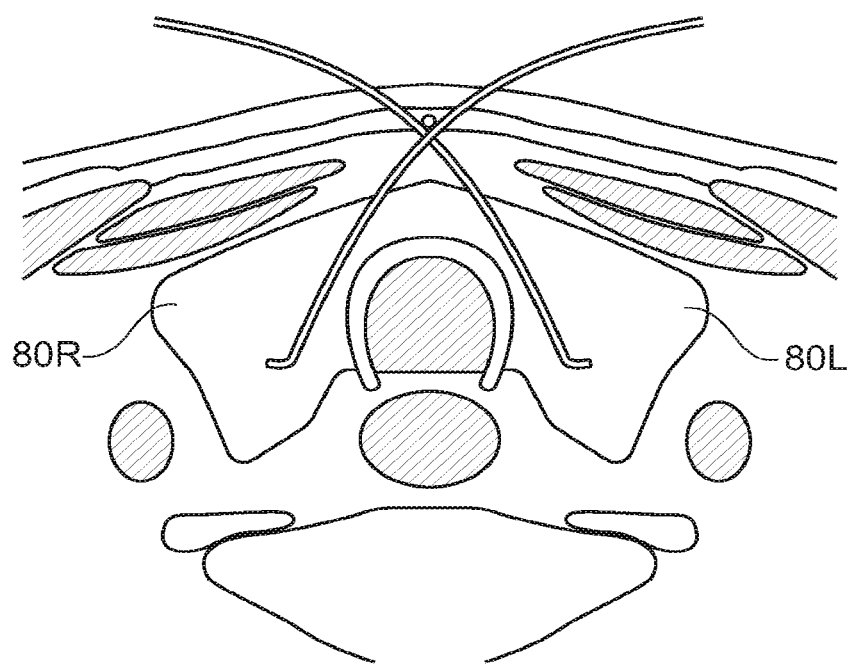

The thyroid—denoted with 90 in FIG. 8—has two lobes 90R and 90L which can be removed separately from each other. When—as illustrated in FIG. 9—only the left lobe 90L is removed, a compartment 80L is formed. When the entire thyroid is removed, two compartments 80R and 80L are formed—as shown in FIG. 10.

Although the compartments 80R and 80L are coherent, in the latter case it is advantageous when each compartment is equipped with a pressure sensor. The signal tubes 30 are then connected preferably jointly to the pressure transducer 16 via a Y connector.

In the shown embodiment for monitoring secondary bleeding after thyroid surgery, basically at least one of the two parameters, viz.

a) the pressure in the postoperative organ compartment, and b) a parameter depicting the expansion of the skin section adjoining the organ compartment which usually also depicts the swelling of a body portion adjoining the organ compartment, is continuously monitored.

In addition, further parameters such as the breathing rate, the blood pressure RR and/or the heart rate and/or the oxygen content in the blood can be taken into consideration.

The detected parameters are evaluated by the ECU/CPU, with the evaluation being performed in such way that critical states are assigned to particular parameter constellations. Accordingly, evaluations such as very low, low, normal, high and very high can be assigned to said different predetermined states, for example based on a fuzzy logic approach.

The analysis logic evaluates the probability of the presence of any health anomaly, i.e. the probability of secondary bleeding in this case, on the basis of the present parameter constellation. After receiving the evaluation, the latter is displayed on the basic unit 30 by a display device, if deemed to be necessary by the logic.

Together with the evaluations, instructions can be output at the display device which can be read partially, continuously or by means of symbols depending on the display device. In the case of display devices which usually are rather small, the instructions can be displayed only partially, whereas a larger display device also permits detailed instructions to be displayed.

Figure 6:
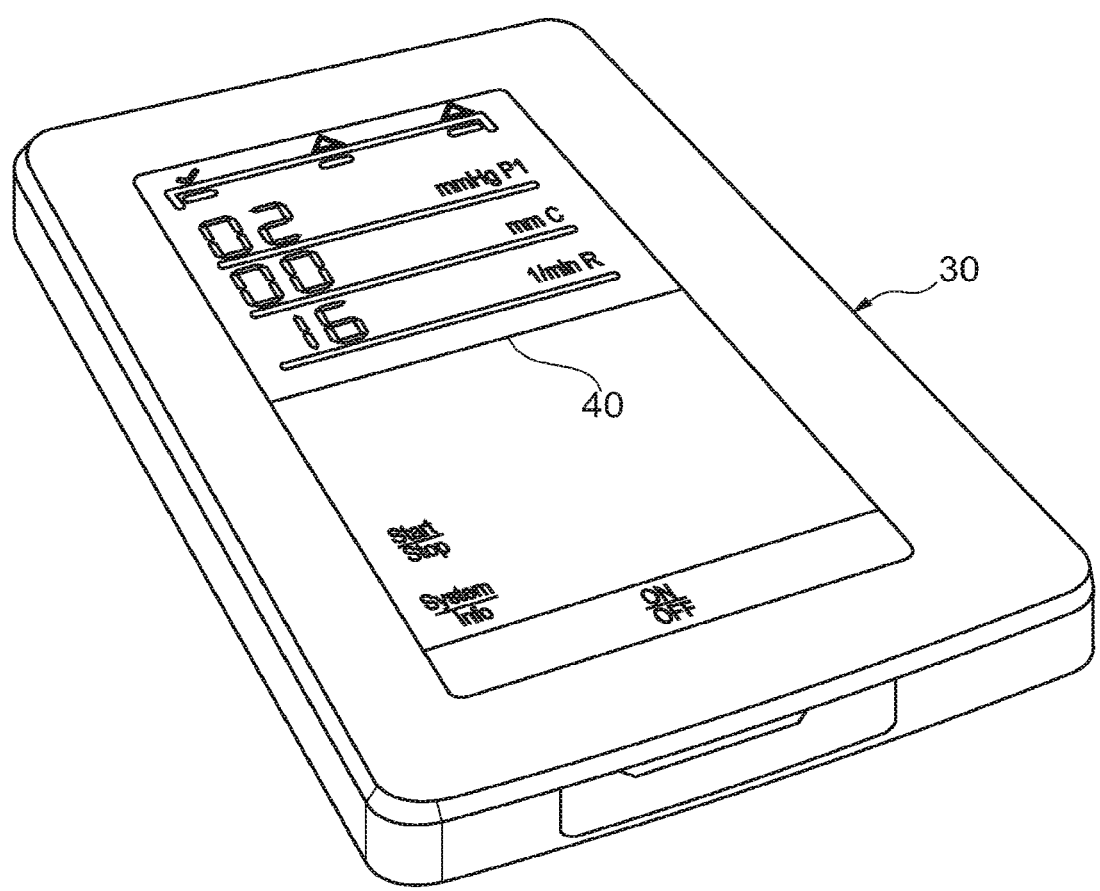
FIG. 6 shows a perspective view of the basic device.

For example, the basic unit 30—as is evident from FIG. 6—in the top line shows the evaluation by a symbol similar to traffic lights. In the lines below the values of the monitored parameters are shown. For example, in one line the compartment pressure is displayed in mmHg, in another line the parameter depicting the expansion of the skin, for example the neck circumference is shown in mm (as illustrated), and in a third line the breathing rate is shown in 1/min. Instead of the expansion in mm, also a percentage increase in the skin expansion close to the operating field, such as the percentage increase in the neck circumference, may be displayed. Also, one-dimensional or multi-dimensional measurement of a swelling due to secondary bleeding of a body section adjoining the operating field may be carried out. For example, two-dimensional measurement of expansion or measuring of the bulge of the skin may be applied.

Instead of the measured values, also merely the states of the measured parameters may be displayed in different stages, such as NON-CRITICAL, TO BE OBSERVED and CRITICAL, even using pictograms.

In further display fields, an indication that all values are non-critical may be displayed, as long as there is no risk for the person to be monitored. If a critical state is established, in said text field an instruction may show, flash or run down. Furthermore, alternately different vital parameters may be displayed in the columns, unless any critical values are detected.

Moreover, the result of the analysis logic is returned to the same again via the processing step P, as vital parameters may considerably deviate from each other depending on the current activity of the person. In this way, the system learns to better distinguish possible non-critical states, such as e.g. idle states, from critical states.

By way of FIGS. 7 to 10 it is evident in which way in patients undergoing thyroid surgery the pressure in the thyroid compartment is detected.

Figure 11:
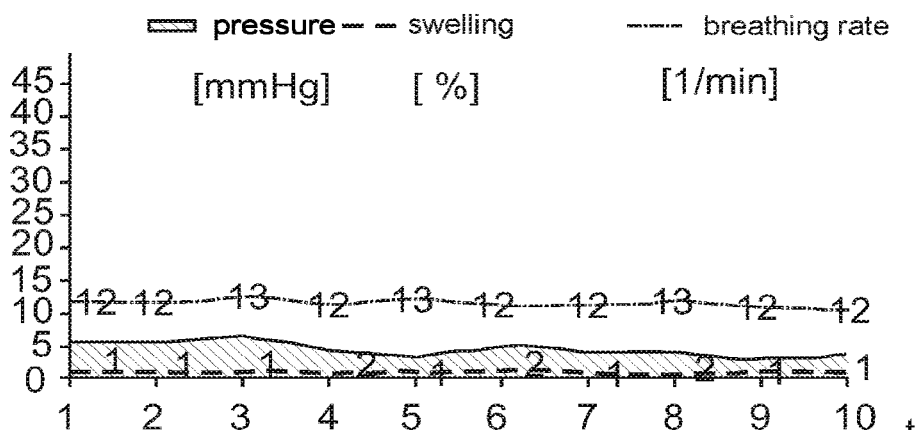
FIGS. 11 to 13 shows exemplary signal diagrams recorded by a system according to the invention.

The system according to the invention operates as follows after the patient has been connected, wherein reference is made to FIGS. 11 to 13 which reproduce concretely taken measurements:

FIG. 11 illustrates the normal curve of the recorded parameter values without any invalidating state occurring. In FIG. 11, above the time intervals 1 to 10 (corresponding to about 5 hours) the compartment pressure in mmHg (orange zone), the percentage variation of the neck circumference (blue curve) as a parameter depicting the swelling of a body section and, resp., the expansion of the skin caused in this way, and the breathing rate (grey curve) in 1/min are displayed.

Although the compartment pressure is varying—depending on the physical activity—within a particular range, the permitted limits of variation set in the device—individualized where necessary—are not exceeded and consequently do not result in an alarm signal. This applies mutatis mutandis to the parameter indicating the swelling of the body region in the vicinity of the thyroid compartment and, resp., the expansion of the respective skin section. Said second parameter serves for additionally protecting the patient. However, it is emphasized that the measurement of only one of said parameters is sufficient to render the system fully operable.

In the shown example embodiment, breathing is additionally monitored. It is evident that this parameter reflects a resting state of the patient. However, it is possible by detecting this parameter to incorporate the state of agitation of the patient (awake, relaxing, panicking, sleeping) in the evaluation.

Figure 12:
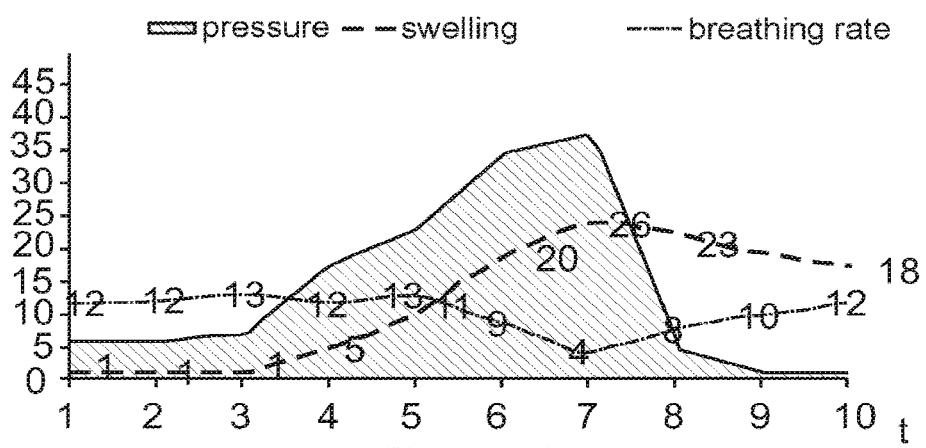

FIG. 12 illustrates the curve of the parameters in the case of acute secondary bleeding. The evaluation shows that the parameters of compartment pressure and neck swelling are increasing simultaneously and synchronously. With a certain time delay the breathing rate starts to decrease. The system can take the decrease of the breathing rate as a reason to reduce the measuring intervals for the two other parameters so that a closer-meshed monitoring takes place to trigger early alarm and to prevent false alarm. In the shown example, after reaching the critical value for either of the parameters of compartment pressure and swelling, a required surgical therapy is initiated and the compartment is relieved. In this way, cessation of breathing could be prevented.

Figure 13:
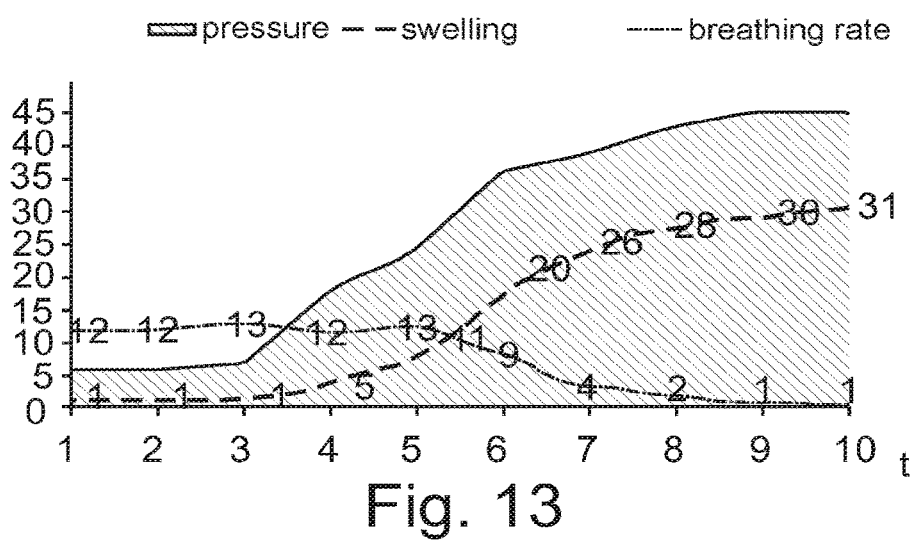

FIG. 13 illustrates the course of the recorded parameter values when secondary bleeding occurs without any rescue measure being initiated. In contrast to the diagram according to FIG. 12, the breathing ceases upon reaching the limits for the parameters of compartment pressure and swelling (asphyxia).

It is resulting from the foregoing description that the subject matter of the invention also is a method which enables early detection of invalidating states of persons such as e.g. postoperative bleeding of a patient, especially secondary bleeding after organ operation. Accordingly, a pressure sensor—for example in the form of a closed balloon member—which is connected to a pressure sensor via a signal tube, e.g. a reporting tube filled with liquid—for example NaCl solution—is inserted into the compartment forming during surgery. The signal tube is inserted by sewing over a particular length, i.e. tightly fastened to the patient. The pressure sensor is connected to a detector unit for continuous detection of the compartment pressure. Alternatively or additionally, another probe for detecting the swelling of a body section adjoining the compartment (neck circumference) which is depicted e.g. by detecting the expansion of the skin section adjoining the organ compartment, may be attached to the patient. Also, further parameters can be simultaneously detected such as a parameter depicting breathing or a parameter as stated in claim 3. The method makes use of a detector unit including a computing unit, an interface and an analysis logic which, on the basis of the at least one present parameter state, displays an evaluation of the probability of the presence of a health anomaly such as the probability of postoperative bleeding. Hence, the method makes use of the system as outlined in the claims.

Of course, deviations from the afore-described example embodiments are possible without leaving the basic idea of the invention.

In this way, it is equally possible to use the system for monitoring postoperative bleedings after different operations. Equally, the measuring probes are not subjected to any restriction as to shape and size thereof.

The signal node may as well be directly integrated in the basic unit.

As a matter of course, it is also possible to forward the detected signals of the measuring probes to the system in a different way, such as wirelessly by means of Bluetooth, infrared or radio communication.

It is further imaginable that the person need not carry the basic unit 30 at his/her hip, he/she may as well carry the same hanging around his/her neck or at his/her arm or leg.

Different modifications of the display device are possible by which the states of health hazards can be displayed. A type of traffic light status lamp with the three colors green, yellow and red is just as imaginable as a display of bars or other elements of different size.

Apart from the fact that the persons to be monitored carry the system with them, the system may just as well be provided at a different location such as at the attending physician, in a hospital or at a monitoring location which is arranged exactly for this purpose.

Also, other parameters exceeding limits which solely or by interaction allow to conclude an invalidating state of a patient may result in the alarm being triggered.

Thus, the invention provides a system for early detection of invalidating states of persons such as e.g. postoperative bleeding of a patient, especially secondary bleeding after organ surgery, comprising a detector unit for continuous detection of plural selected parameters. The detector unit includes sensors, a computing unit, an interface and an analysis logic which, on the basis of the present parameter states, evaluates the probability of the presence of a health anomaly, e.g. the probability of postoperative bleeding. The pressure in the postoperative organ compartment and/or a parameter which represents the expansion of the skin section adjoining the organ compartment is selected as the selected parameter.

The invention claimed is:

1. A system configured for early detection of internal bleeding of a patient, the system comprising:
   a pressure sensor adapted to continuously detect a pressure in a body compartment of the patient that is being monitored for internal bleeding, the pressure sensor including a balloon or an end cap inserted into the body compartment of the patient and connected to a signal tube filled with pressure-transferring fluid;
   processing circuitry including analysis logic that compares at least one parameter including pressure detected by the pressure sensor against a predetermined parameter threshold at which internal bleeding by the patient has been determined to be probable and provides an output indicating whether internal bleeding by the patent is probable; and a display device comprising display processing circuitry and a display, the display processing circuitry configured to display the output of the analysis logic on the display, wherein when the analysis logic determines that internal bleeding is probable, the analysis logic triggers an alarm for display on the display by the display device, and wherein the processing circuitry sets permitted limits of variation of the pressure detected by the pressure sensor whereby the analysis logic does not trigger the alarm when the pressure detected by the pressure sensor varies within the permitted limits of variation.

2. The system of claim 1, further comprising a strain gauge that detects a breathing rate of the patient, wherein when a decrease in the patient's breathing rate is detected, a measuring interval for at least the pressure in the body compartment is reduced.

3. The system of claim 1, wherein the analysis logic includes a neural network that is trained on parameter constellations of a plurality of parameters including the pressure in the body compartment to recommend, during use, a course of action in response to a detected parameter constellation.

4. The system of claim 3, wherein the processing circuitry comprises a processing unit that evaluates the at least one parameter to assign critical states to particular parameter constellations as the predetermined parameter threshold.

5. The system of claim 3, wherein the analysis logic outputs instructions for treatment of the patient for display on the display in accordance with the recommended course of action.

6. The system of claim 3, wherein the neural network is trained using individual medical data corresponding to a type of surgical intervention and related to a health state of the patient, and wherein the analysis logic recommends the course of action in accordance with the health state of the patient.

7. The system of claim 1, wherein measurement time intervals for the at least one parameter are adapted to a current health state of the patient, the current health state including at least one of anatomic, surgery-specific, or patient-specific variables associated with the patient.

8. The system of claim 1, wherein the analysis logic comprises a fuzzy logic module that applies a fuzzy logic approach.

9. The system of claim 8, wherein the fuzzy logic module is individually calibrated according to a health state of the patient.

10. The system of claim 1, wherein the predetermined parameter threshold is varied for the pressure in the body compartment of the patient in accordance with individual medical data of the patient.

11. The system of claim 1, wherein the analysis logic is adaptive to habits and a rhythm of the patient during use.

12. The system of claim 1, wherein the display comprises a lamp configured to display in different colors in accordance with a health state as a result of comparison of the at least one parameter against the predetermined parameter threshold.

13. The system of claim 1, further comprising a transmitter configured to forward the output of the analysis logic to a central unit, the output including at least one selected result of evaluation or instruction for treating the patient.

14. The system of claim 13, further comprising a position detector, wherein the transmitter is configured to forward to the central unit a spatial and/or geographic position of the patient as determined by the position detector.

15. The system of claim 1, wherein the body compartment of the patient is formed from at least partial removal of an organ and the internal bleeding being monitored is postoperative bleeding.

16. The system of claim 15, wherein the body compartment of the patient comprises a thyroid compartment of the patient.

17. The system of claim 1, further comprising a tension sensor that detects expansion of skin of the patient at a skin section located in a vicinity of the body compartment of the patient and provides tension parameters to the analysis logic.

18. The system of claim 1, further comprising a neck expansion sensor that detects expansion of a circumference of a neck of the patient and provides neck expansion parameters to the analysis logic.

19. The system of claim 1, wherein the at least one parameter includes at least one of breathing rate, blood pressure resting rate, hear rate, or oxygen content in blood of the patient.

20. The system of claim 1, further comprising a signal node that receives signals of different signal lines including the at least one parameter and a separate device that communicates with the signal node and includes the processing circuitry to receive, process, and evaluate the signals from the signal node and the display to display processed outputs.

* * * * *